US011788067B2

(12) United States Patent
Meyers et al.

(10) Patent No.: US 11,788,067 B2
(45) Date of Patent: Oct. 17, 2023

(54) PRODUCTION OF A HORSERADISH PEROXIDASE-IGG FUSION PROTEIN

(71) Applicant: University of Cape Town, Cape Town (ZA)

(72) Inventors: Ann Elizabeth Meyers, Plumstead (ZA); Edward Peter Rybicki, Cape Town (ZA); Inga Isabel Hitzeroth, Cape Town (ZA)

(73) Assignee: University of Cape Town, Cape Town (ZA)

( * ) Notice: Subject to any disclaimer, the term of this patent is extended or adjusted under 35 U.S.C. 154(b) by 0 days.

(21) Appl. No.: 16/304,205

(22) PCT Filed: May 23, 2017

(86) PCT No.: PCT/IB2017/053029
§ 371 (c)(1),
(2) Date: Nov. 23, 2018

(87) PCT Pub. No.: WO2017/203426
PCT Pub. Date: Nov. 30, 2017

(65) Prior Publication Data
US 2020/0339963 A1 Oct. 29, 2020

(30) Foreign Application Priority Data
May 25, 2016 (GB) ..................................... 1609235

(51) Int. Cl.
*C12N 9/08* (2006.01)
*C07K 16/42* (2006.01)

(52) U.S. Cl.
CPC ........ *C12N 9/0065* (2013.01); *C07K 16/4283* (2013.01); *C12Y 111/01007* (2013.01); *C07K 2317/622* (2013.01); *C07K 2319/21* (2013.01); *C07K 2319/61* (2013.01)

(58) Field of Classification Search
None
See application file for complete search history.

(56) References Cited

U.S. PATENT DOCUMENTS

| 5,910,573 A | 6/1999 | Plückthun et al. |
| 6,358,733 B1 | 3/2002 | Motwani et al. |
| 2005/0059053 A1 | 3/2005 | Fischer et al. |
| 2011/0098448 A1 | 4/2011 | Korth et al. |

FOREIGN PATENT DOCUMENTS

| WO | WO 2001/42308 | 6/2001 |
| WO | WO 2005/014650 | 2/2005 |
| WO | WO 2007/014743 | 2/2007 |
| WO | WO 2008/151405 | 12/2008 |
| WO | WO 2015/098113 | 7/2015 |

OTHER PUBLICATIONS

Min et al.,"A Recombinant Secondary Antibody Mimic as a Target-specific signal amplifier and an antibody immobilizer in immunoassays", Scientific Reports, 6:24159. doi: 10.1038/srep24159 Apr. 11 (Year: 2016).*
Casey et al., "Purification of bacterially expressed single chain Fv antibodies for clinical applications using metal chelate chromatography", Journal of Immunological Methods 179: 106-116 (Year: 1995).*
Linder et al., "Specific detection of his-tagged proteins with recombinant anti-his tag scFv-phosphatase or scFv-phage fusions", BioTechniques 22: 140-149 (January) (Year: 1997).*
Koliasnikov et al.,"Recombinant production of horseradish peroxidase conjugates with Fab antibodies in Pichia Pastoris for analytical applications", Acta Naturae vol. 3, No. 3(10): 85-92 (Year: 2011).*
Petruccelli et al., "A KDEL-tagged monoclonal antibody is efficiently retained in the endoplasmic reticulum in leaves, but is both paritally secreted and sorted to protein storage vacuoles in seeds", Plant Biotechnology Journal 4: 511-527 (Year: 2006).*
Muraki and Honda, "Efficient production of a human Fas receptor extracellular domain-human IgG1 heavy chain Fc domain fusion protein using baculovirus/silkworm expression system", Protein Expression and Purifcation 73: 209-216 (Year: 2010).*
Griep et al., *pSKAP/S: An Expression Vector for the Production of Single-Chain Fv Alkaline Phosphatase Fusion Proteins*, 16 Protein Expression and Purification 63-69 (1999).
Koliasnikov et al., *Recombinant Production of Horseradish Peroxidase Conjugates with Fab Antibodies in Pichia pastoris for Analytical Applications*, 3(10) Acta Naturae 85-92 (2011).
Martin et al., A simple vector system to improve performance and utilisation of recombinant antibodies, 6(46) BMC Biotechnology 1-15 (Dec. 7, 2006).
Sasajima et al., *Expression of antibody variable region-human alkaline phosphatase fusion proteins in mammalian cells*, 361 Journal of Immunological Methods 57-63 (2010).
Suzuki et al., *Construction, Bacterial Expression, and Characterization of Hapten-Specific Single-Chain Fv and Alkaline Phosphatase Fusion Protein*, 122 J. Biochem 322-329 (1997).
Bird et al., *Single chain antibody variable regions*, 9 TIBTECH 132-137 (Apr. 1991).

\* cited by examiner

*Primary Examiner* — Anand U Desai
(74) *Attorney, Agent, or Firm* — Panitch Schwarze Belisario & Nadel LLP; Erin M. Dunston

(57) ABSTRACT

The present invention relates to a fusion protein consisting of a scFv linked to a horseradish peroxidase enzyme or to an alkaline phosphatase enzyme by a peptide linker. The fusion protein also includes a histidine tag and optionally an endoplasmic reticulum retention signal. The invention also includes nucleic acids encoding the fusion protein, expression vectors containing the nucleic acids, plant cells transformed with the expression vectors and methods of producing the fusion proteins of the invention.

9 Claims, 19 Drawing Sheets
Specification includes a Sequence Listing.

| ER signal | Mature HRP protein | Linker | scFv | SEKDEL | His |
Figure 1
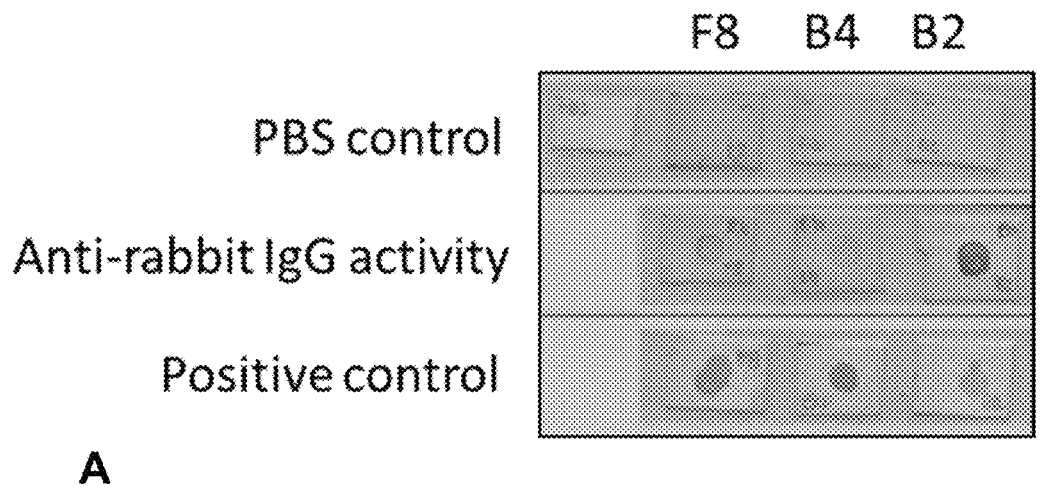
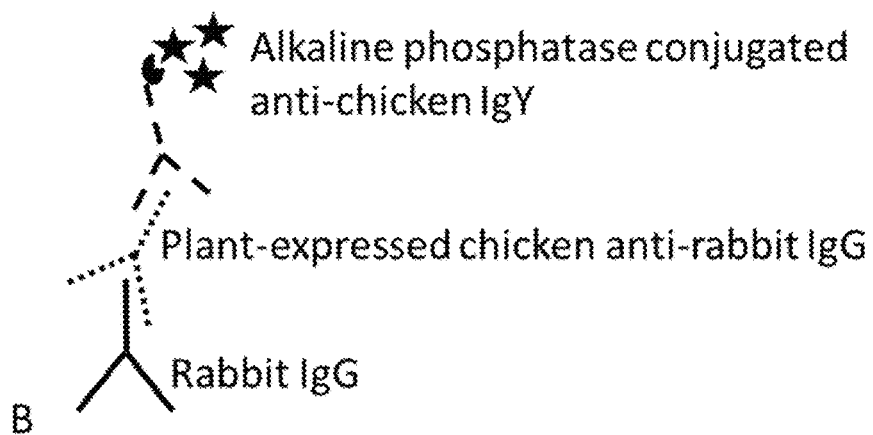
Figure 2

Anti-L1 (Gardasil)    Anti-L2 (D42 rabbit serum)

M – molecular weight marker
C – commercial anti-rabbit-HRP
P – plant HRP-IgG

Rabbit anti-H1tr (in-house)

M – molecular weight marker
C – commercial anti-rabbit-HRP
-ve – no H1tr (plant extract)
P – plant HRP-IgG (B2_2)
P – plant HRP-IgG (Be_2_SEKDEL)

Rabbit anti-BFDV (in-house)

M – molecular weight marker
C – commercial anti-rabbit-HRP
-ve – no BFDV (plant extract)
P – plant HRP-IgG

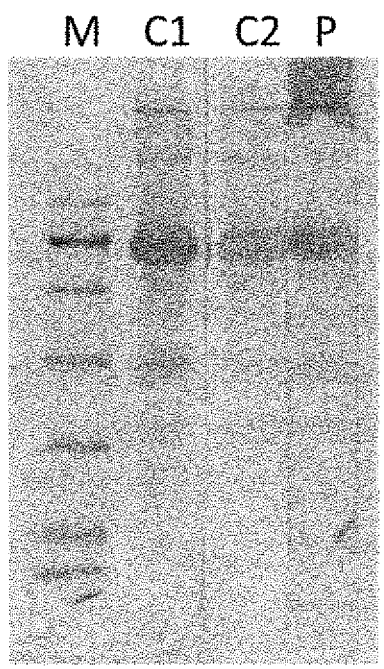
M – molecular weight marker
C1 – commercial anti-rabbit-HRP
C2 – different anti-rabbit-HRP
P – plant HRP-IgG
Rabbit anti-GOX (Abcam)
Figure 6 contd.

1 – M (Benchmark Invitrogen #10748010) 5μl
2 – Marker leaked!
3 – F2 30μl
4 – F2 leaked
5 – F16 30μl
6 – F17 30μl
7 – F18 30μl
8 – F19 30μl 1 – M (Benchmark Invitrogen # 10748010) 5µl
2 – F2 40µl
3 – F7 40 µl
4 – F14 40 µl
5 – F15 40µl
6 – F16 40 µl
7 – F17 40µl
8 – F18 40 µl
9 – F19 40 µl Western blot of GOX protein – 10-02-2016

Rabbit anti-GOX primary antibody

M – molecular weight marker
C – commercial anti-rabbit-HRP
P – plant produced HRP-IgG
-ve – negative control

A

B

| 1 | Positive control- crude extract | 9 | Marker |
|---|---|---|---|
| 2 | Negative control- crude plant material (not infiltrated) | 10 | Flow through |
| 3 | 0-40% AmSO$_4$ supernatant | 11 | Wash 1 |
| 4 | 0-40% AmSO$_4$ pellet | 12 | Wash 2 |
| 5 | 40-60% AmSO$_4$ supernatant | 13 | Wash 3 |
| 6 | - | 14 | Elution 1 |
| 7 | 40-60% AmSO$_4$ pellet after dialysis | 15 | Elution 2 |
| 8 | 40-60% AmSO$_4$ pellet after dialysis and centrifugation | 16 | Elution 3 |

| 1 | DE 30ul |
| 2 | Crude extract 30ul |
| 3 | Marker 5ul |
| 4 | Lyophilised DE (1/10 dilution) 30ul |
| 5 | DEcp (1/20 dilution) 30ul |
| 6 | DEcs 30ul |
| 7 | DE 30 ul |
| 8 | Crude extract 30ul |
| 9 | His marker 5ul |
| 10 | Negative control (plant only) |

PRODUCTION OF A HORSERADISH PEROXIDASE-IGG FUSION PROTEIN

BACKGROUND OF THE INVENTION

The present invention relates to a fusion protein consisting of a scFv linked to a horseradish peroxidase enzyme or to an alkaline phosphatase enzyme by a peptide linker. The fusion protein also includes a histidine tag and optionally an endoplasmic reticulum retention signal. The invention also includes nucleic acids encoding the fusion protein, expression vectors containing the nucleic acids, plant cells transformed with the expression vectors and methods of producing the fusion proteins of the invention.

Horseradish (*Armoracia rusticana*, syn. *Cochlearia armoracia*) is a perennial plant of the Brassicaceae family (which also includes mustard, wasabi, broccoli, and cabbage). It is a root vegetable used as a spice.

Horseradish peroxidase (HRP) is an enzyme isolated from horseradish (*Armoracia rusticana*) roots and belongs to the ferroprotoporphyrin group of peroxidases. The HRP protein is a single chain polypeptide which contains four disulfide bridges.

The HRP enzyme is used extensively in biochemistry applications primarily for its ability to amplify a weak signal and increase detectability of a target molecule. It is a metalloenzyme with many isoforms, of which the most studied isoform is type C.

HRP is a 44,173.9-dalton glycoprotein with 6 lysine residues which can be conjugated to a molecule. It produces a coloured, fluorimetric, or luminescent derivative of the conjugated molecule when incubated with a proper substrate, allowing it to be detected and quantified.

Alkaline phosphatase (AP) is a homodimeric protein enzyme of 86 kilo-daltons, containing two zinc atoms crucial for its catalytic function. Each monomer includes a zinc atom. AP is active at alkaline pH.

AP is found in many organisms, including prokaryotes and eukaryotes. The various forms have the same general function but may have different structural forms that are suitable to the environment in which they function.

The presence of the HRP or AP enzyme, or conjugates thereof, is made visible using a substrate that, when oxidized by HRP or AP using hydrogen peroxide as the oxidizing agent, yields a characteristic change that is detectable by spectrophotometric methods.

HRP is also commonly used in techniques such as ELISA and immunohistochemistry due to its monomeric nature and the ease with which it produces coloured products. Traditionally, commercially available HRP or AP-linked secondary antibodies are usually made by the chemical conjugation of HRP or AP to an antibody. This can result in non-homogenous compositions of the product, as well as reduced activity of the HRP or AP and the antibody, and stoichiometry is often not the desired 1:1 ratio of marker protein to antibody—all of which affect ELISA and western blot specificity and sensitivity. With the genetic fusion and expression of recombinantly-produced marker-antibody products, these problems are alleviated. A possible solution would be to produce the fusion proteins in *E. coli*, however, the problem with this is that the product is not soluble—the lack of post translational glycosylation in *E. coli* leads to the aggregation of expressed recombinant protein in inclusion bodies and therefore hinders HRP activity. Some research has been carried out to produce recombinant genetically fused HRP-antibody (the Fab fragment of an antibody against atrazine (Koliasnikov et al 2011)) in *Pichia pastoris* to alleviate the solubility problem.

The present invention results in the production of a recombinant fusion product consisting of the marker protein (HRP or AP) fused to a single chain variable fragment (scFv) which is an even smaller region of the antibody than the Fab fragment described above. Further, the present invention relies on the fusion protein being produced in plants.

SUMMARY OF THE INVENTION

The present invention relates to a fusion protein consisting of a scFv linked to a horseradish peroxidase enzyme or to an alkaline phosphatase enzyme by a peptide linker. The fusion protein also includes a histidine tag and optionally an endoplasmic reticulum retention signal.

According to a first aspect of the invention there is provided for a fusion protein comprising a polypeptide encoding a horseradish peroxidase or an alkaline phosphatase, a peptide linker, a polypeptide encoding a scFv, optionally an endoplasmic reticulum retention signal and a histidine tag.

A second aspect of the invention provides for a fusion protein comprising a formula selected from formula I or formula II:

$$X_1\text{-}X_2\text{-}X_3\text{-}(X_4)_n\text{-}X_5 \qquad (I)$$

$$X_3\text{-}X_2\text{-}X_1\text{-}(X_4)_n\text{-}X_5 \qquad (II)$$

wherein $X_1$ is a polypeptide encoding a horseradish peroxidase or an alkaline phosphatase, $X_2$ is a peptide linker, $X_3$ is a polypeptide encoding a scFv, $X_4$ is an endoplasmic reticulum retention signal, $X_5$ is a histidine tag and n is 0 or 1.

In one embodiment of the invention the polypeptide encoding the horseradish peroxidase or the alkaline phosphatase includes an endoplasmic reticulum targeting signal. Preferably, the horseradish peroxidase or alkaline phosphatase includes an N-terminal endoplasmic reticulum targeting sequence.

In another embodiment of the invention the scFv has immunoglobulin activity selected from anti-mouse, anti-donkey, anti-rabbit, anti-horse, anti-human, anti-chicken, anti-goat or anti-sheep activity. Preferably, the the scFv has anti-rabbit activity.

In a further embodiment the endoplasmic reticulum retention signal is selected from the group consisting of HDEL (SEQ ID NO:3), KDEL (SEQ ID NO:2), SEKDEL(SEQ ID NO:1) or variants thereof. However, those of skill in the art will appreciate that the endoplasmic reticulum retention signal may be selected from endoplasmic reticulum signals known in the art.

In order to assist with the purification of the fusion protein it will be appreciated that the fusion protein includes a histidine tag. Preferably, the histidine tag is a 6× histidine tag.

A further embodiment of the invention may entail including a human IgG1 heavy chain constant region and a human IgG1 light chain constant region, linked to the scFv. It will be appreciated that inclusion of the constant regions will allow for Fc effector function.

A second aspect of the invention provides for a nucleic acid molecule encoding the fusion protein of the invention.

A third aspect provides for an expression vector comprising the nucleic acid molecule encoding the fusion protein of the invention.

A further aspect of the invention provides for a plant cell transformed with the expression vector comprising the nucleic acid molecule encoding the fusion protein of the invention.

In yet another aspect of the invention there is provided for a method for producing a fusion protein of the invention comprising expressing the fusion protein in a plant cell and recovering the fusion protein from the plant cell.

In a preferred embodiment the plant cell is a *Nicotiana* sp. plant cell.

I further aspect of the invention provides for a kit comprising a fusion protein of the invention or an expression vector as described herein.

BRIEF DESCRIPTION OF THE FIGURES

Non-limiting embodiments of the invention will now be described by way of example only and with reference to the following figures:

FIG. 1: Exemplary schematic representation of HRP-Ig fusion construct. The fusion construct is comprised of: 1—the native HRP N-terminal signal sequence responsible for protein-targeting to the ER (ER signal); 2—the mature portion of HRP (mature HRP protein); 3—a rigid α-helical linker (linker); 4—the chicken-derived IgY scFv (scFv); 5—a SEKDEL ER retention signal (SEQ ID NO:1) resulting in ER protein accumulation (either present or not) (SEKDEL—SEQ ID NO:1); and 6—a C-terminal His-tag for downstream protein purification (his).

FIG. 2: (A) Dot blot confirming anti-rabbit IgG binding activity of plant-expressed chicken-derived IgY scFvs (B2, B4 and F8). PBS controls showed no binding (absence of colour development), while a colorimetric result colour could be seen developing where scFvs had bound rabbit IgG. Positive controls confirmed that scFvs were present in the plant extract. (B) Schematic representation of the components used to detect scFv activity in the dot blot. Initially, rabbit IgG is bound to the membrane, following this, plant-expressed chicken-derived IgY scFvs are added which recognise and bind to the rabbit IgG. The bound scFvs can then be detected using an alkaline phosphatase conjugated anti-chicken IgY. The alkaline phosphatase is responsible for colour development when substrate is added.

DETAILED DESCRIPTION OF THE INVENTION

Figure 3:
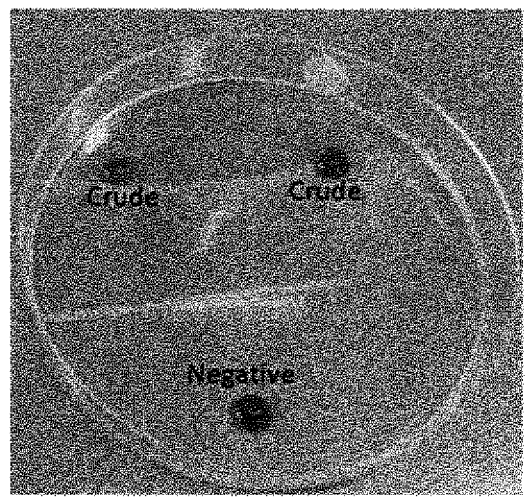
FIG. 3: Rapid HRP test showing presence of HRP in crude leaf extracts infiltrated with HRP_B2_SEKDEL (left hand side crude) and HRP_B2 (right hand side crude) and lack of presence in crude leaf extracts infiltrated with empty construct (negative).
Figure 4:
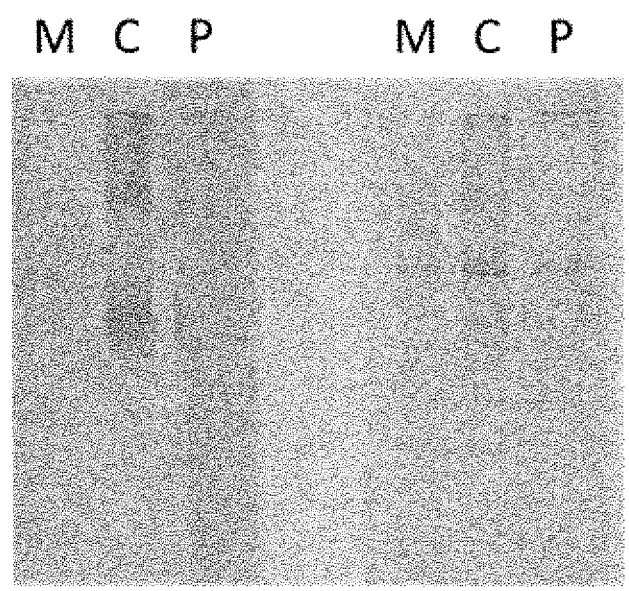
FIG. 4: Western blot of HPV16 L1-L2 protein probed with anti-L1 (Gardasil) at a 1:2000 dilution and anti-L2 rabbit serum at a 1:1000 dilution and detected with either commercially available anti-rabbit-HRP (C) or crude plant-produced HRP_B2_SEKDEL scFv

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

The present invention relates to plant-produced HRP-fused or AP-fused single chain variable fragment (scFv) (the "fusion protein") which has anti-rabbit immunoglobulin (Ig) activity. However, it will be appreciated that the scFv may have anti-mouse, anti-donkey, anti-horse, anti-chicken, anti-goat or anti-sheep immunoglobulin activity. The fusion protein of the invention can be used as a secondary antibody in western blotting and ELISA.

The term "single chain antibody fragment" (scFv) or "antibody fragment" as used herein means a polypeptide containing a variable light (VL) domain linked to a variable heavy (VH) domain, containing all six CDR's which are linked by a peptide linker (L). The order of the VL and VH domains can be joined and represented as VH-L-VL or VL-L-VH. The variable regions of the light chain and heavy chain of an antibody interact with an antigen.

To prepare a vector containing the DNA sequence for a scFv, a source of the genes encoding for these regions is required. The appropriate DNA sequence can be obtained from published sources or can be obtained by standard procedures known in the art. For instance, Kabat et al., Sequences of Proteins of Immunological Interest 4th ed., (1991), published by The U.S. Department of Health and Human Services, discloses sequences of most of the antibody variable regions which have been described to date.

Alternatively, when the genetic sequence is unknown, it is generally possible to utilize cDNA sequences obtained from mRNA by reverse transcriptase mediated synthesis as a source of DNA to clone into a vector. For scFv's, the source of mRNA can be obtained from a wide range of hybridomas. Hybridomas secreting monoclonal antibodies reactive with a wide variety of antigens are usable in the present invention. These cell lines and others of similar nature can be utilized as a source of mRNA coding for the variable domains or to obtain antibody protein to determine amino acid sequence of the monoclonal antibody itself.

Variable regions of antibodies can also be derived by immunizing an appropriate vertebrate, normally a domestic animal, and most conveniently a mouse, donkey, rabbit, horse, chicken, goat or sheep may be immunized with an immunogen. The immunogen will be the antigen of interest. The immunization may be carried out conventionally with one or more repeated injections of the immunogen into the host animal, normally at two to three week intervals. Usually, three days after the last challenge, the spleen is removed and dissociated into single cells to be used for cell fusion to provide hybridomas from which mRNA can readily be obtained by standard procedures known in the art.

When an antibody of interest is obtained, and only its amino acid sequence is known, it is possible to reverse translate the sequence.

To form the antibody fragments of the present invention, it is necessary to have a suitable peptide linker. Suitable linkers for joining the VH and VL domains are those which allow the VH and VL domains to fold into a single polypeptide chain which will have a three dimensional structure very similar to the original structure of a whole antibody and thus maintain the binding specificity of the whole antibody from which the scFv fragment is derived. Suitable linkers for linking the scFvs are those which allow the linking of two or more scFvs such that the VH and VL domains have a three dimensional structure which maintains the binding specificity of the whole antibody from which the immunoglobulin fragment is derived. Linkers are known in the art and for the sake of the present invention any linker may be used.

ScFv antibodies offer several advantages over monoclonal antibodies generated by hybridoma technology, in that scFv antibodies can be rapidly and economically produced, resulting in antibodies that are both functionally active and genetically stable.

As used herein, the terms "single-chain Fv" and "scFv" are used interchangeably and mean a polypeptide comprising the VH and VL domains of antibody, wherein these domains are connected by a polypeptide linker between the VH and VL domains into a single polypeptide chain. The linker enables the scFv to form the desired structure for epitope binding.

It will be appreciated that the scFv of the invention can be converted to a full-length antibody by fusing it to human IgG1 heavy and light chain constant regions in order to allow for Fc region effector functions. The full length antibody may be made by cloning the scFv-HRP or scFv-AP into a vector which facilitates the formation of a full length antibody. The scFv-HRP or scFv-AP will be cloned in a position such that a full length recombinant antibody presenting the scFv-HRP or scFv-AP will be generated. Activity of the HRP or AP may be measured using a guaiacol assay and functionality of the fusion protein as a secondary antibody may be tested against the same set of rabbit antibodies that were used to test functionality of the scFv HRP fusion protein alone, as described herein.

The fusion protein of the invention has many benefits over similar products as the currently available HRP-linked anti-rabbit secondary antibodies are produced in mammalian cells and therefore are subject to strict regulations with regard to importation, and are also less desirable as they are derived from animal cells and there is always the chance of contamination with other animal proteins. In addition, HRP-linked anti-rabbit secondary antibodies (or AP-linked anti-rabbit secondary antibodies) produced in mammalian cells are extremely expensive. Production of HRP-Ig or AP-Ig in plants would mean that the product is devoid of any possible mammalian cell contaminants and is cheaper to produce, therefore providing a more cost-effective reagent to the end-user.

A fusion protein according to the invention includes, without limitation, a fusion protein including the amino acid sequence of a mature HRP protein or a mature AP protein, including an N-terminal ER targeting sequence, a linker, an scFv, optionally including an ER retention signal, and a histidine tag. The scFv may be fused to the C-terminal of the HRP with the linker. Alternatively, the HRP and scFv gene sequences may be swapped around so that the scFv is fused to the N-terminal of the HRP peptide and the linker is inserted between the histidine tag and HRP. This may improve yields and also aid in purification, by facilitating efficient binding on the affinity purification column. Further, if the fusion protein includes AP as opposed to HRP the scFV may be fused to the C-terminal of the AP with the linker. Alternatively, the AP and scFv gene sequences may be swapped around so that the scFv is fused to the N-terminal of the AP peptide and the linker is inserted between the histidine tag and AP.

A "protein," "peptide" or "polypeptide" is any chain of two or more amino acids, including naturally occurring or non-naturally occurring amino acids or amino acid analogues, irrespective of post-translational modification (e.g., glycosylation or phosphorylation).

The terms "nucleic acid" or "nucleic acid molecule" encompass both ribonucleic acids (RNA) and deoxyribonucleic acids (DNA), including cDNA, genomic DNA, and synthetic DNA. The nucleic acid may be double-stranded or single-stranded. Where the nucleic acid is single-stranded, the nucleic acid may be the sense strand or the antisense strand. A nucleic acid molecule may be any chain of two or more covalently bonded nucleotides, including naturally occurring or non-naturally occurring nucleotides, or nucleotide analogs or derivatives. By "RNA" is meant a sequence of two or more covalently bonded, naturally occurring or modified ribonucleotides. The term "DNA" refers to a sequence of two or more covalently bonded, naturally occurring or modified deoxyribonucleotides. By "cDNA" is meant a complementary or copy DNA produced from an RNA template by the action of RNA-dependent DNA polymerase (reverse transcriptase).

Accordingly, a "cDNA clone" refers to a duplex DNA sequence which is complementary to an RNA molecule of interest, and which is carried in a cloning vector. The term "complementary" refers to two nucleic acids molecules, e.g., DNA or RNA, which are capable of forming Watson-Crick base pairs to produce a region of double-strandedness between the two nucleic acid molecules. It will be appreciated by those of skill in the art that each nucleotide in a nucleic acid molecule need not form a matched Watson-Crick base pair with a nucleotide in an opposing complementary strand to form a duplex. One nucleic acid molecule is thus "complementary" to a second nucleic acid molecule if it hybridizes, under conditions of high stringency, with the second nucleic acid molecule. A nucleic acid molecule according to the invention includes both complementary molecules.

In some embodiments, a fusion protein of the invention may include, without limitation, a polypeptide including an amino acid sequence comprising a mature HRP or a mature AP protein, including an N-terminal ER targeting sequence, a linker, a scFv, an ER retention signal (which may be absent) and a histidine tag. Another embodiment of the invention includes, without limitation, nucleic acid molecules encoding the aforementioned fusion proteins.

As used herein a "substantially identical" sequence is an amino acid or nucleotide sequence that differs from a reference sequence only by one or more conservative substitutions, or by one or more non-conservative substitutions, deletions, or insertions located at positions of the sequence that do not destroy or substantially reduce the antigenicity of the expressed fusion protein or of the polypeptide encoded by the nucleic acid molecule. Alignment for purposes of determining percent sequence identity can be achieved in various ways that are within the knowledge of those with skill in the art. These include using, for instance, computer software such as ALIGN, Megalign (DNASTAR), CLUSTALW or BLAST software. Those skilled in the art can readily determine appropriate parameters for measuring alignment, including any algorithms needed to achieve maximal alignment over the full length of the sequences being compared. In one embodiment of the invention there is provided for a polypeptide or polynucleotide sequence that has at least about 80% sequence identity, at least about 90% sequence identity, or even greater sequence identity, such as about 95%, about 96%, about 97%, about 98% or about 99% sequence identity to the sequences described herein.

Alternatively, or additionally, two nucleic acid sequences may be "substantially identical" if they hybridize under high stringency conditions. The "stringency" of a hybridisation reaction is readily determinable by one of ordinary skill in the art, and generally is an empirical calculation which depends upon probe length, washing temperature, and salt concentration. In general, longer probes required higher temperatures for proper annealing, while shorter probes require lower temperatures. Hybridisation generally depends on the ability of denatured DNA to re-anneal when complementary strands are present in an environment below their melting temperature. A typical example of such "stringent" hybridisation conditions would be hybridisation carried out for 18 hours at 65° C. with gentle shaking, a first wash for 12 min at 65° C. in Wash Buffer A (0.5% SDS; 2×SSC), and a second wash for 10 min at 65° C. in Wash Buffer B (0.1% SDS; 0.5% SSC).

In one embodiment of the invention, the fusion proteins may be prepared by, for instance, inserting, deleting or replacing nucleic acids at any position of the nucleic acid molecule encoding the fusion protein.

Those skilled in the art will appreciate that polypeptides, peptides or peptide analogues can be synthesised using standard chemical techniques, for instance, by automated synthesis using solution or solid phase synthesis methodology. Automated peptide synthesisers are commercially available and use techniques known in the art. Polypeptides, peptides and peptide analogues can also be prepared from their corresponding nucleic acid molecules using recombinant DNA technology.

In some embodiments, the nucleic acid molecules of the invention may be operably linked to other sequences. By "operably linked" is meant that the nucleic acid molecules encoding the fusion proteins of the invention and regulatory sequences are connected in such a way as to permit expression of the fusion proteins when the appropriate molecules are bound to the regulatory sequences. Such operably linked sequences may be contained in vectors or expression constructs which can be transformed or transfected into host cells for expression. It will be appreciated that any vector can be used for the purposes of expressing the fusion proteins of the invention.

The term "recombinant" means that something has been recombined. When used with reference to a nucleic acid construct the term refers to a molecule that comprises nucleic acid sequences that are joined together or produced by means of molecular biological techniques. The term "recombinant" when used in reference to a protein or a polypeptide refers to a protein or polypeptide molecule which is expressed from a recombinant nucleic acid construct created by means of molecular biological techniques. Recombinant nucleic acid constructs may include a nucleotide sequence which is ligated to, or is manipulated to become ligated to, a nucleic acid sequence to which it is not ligated in nature, or to which it is ligated at a different location in nature. Accordingly, a recombinant nucleic acid construct indicates that the nucleic acid molecule has been manipulated using genetic engineering, i.e. by human intervention. Recombinant nucleic acid constructs may be introduced into a host cell by transformation. Such recombinant nucleic acid constructs may include sequences derived from the same host cell species or from different host cell species.

The term "vector" refers to a means by which polynucleotides or gene sequences can be introduced into a cell. There are various types of vectors known in the art including plasmids, viruses, bacteriophages and cosmids. Generally polynucleotides or gene sequences are introduced into a vector by means of a cassette. The term "cassette" refers to a polynucleotide or gene sequence that is expressed from a vector, for example, the polynucleotide or gene sequences encoding the fusion proteins of the invention. A cassette generally comprises a gene sequence inserted into a vector, which in some embodiments, provides regulatory sequences for expressing the polynucleotide or gene sequences. In other embodiments, the vector provides the regulatory sequences for the expression of the fusion protein. In further embodiments, the vector provides some regulatory sequences and the nucleotide or gene sequence provides other regulatory sequences. "Regulatory sequences" include but are not limited to promoters, transcription termination sequences, enhancers, splice acceptors, donor sequences, introns, ribosome binding sequences, poly(A) addition sequences, and/or origins of replication. For the purposes of the present invention an expression cassette is preferably used for the expression of the fusion protein of the invention.

As mentioned the fusion protein according to the invention includes, without limitation, an amino acid sequence of a mature HRP protein or a mature AP protein, including an N-terminal ER targeting sequence, a linker, an scFv, an ER retention signal and a histidine tag. It will be appreciated that an expression cassette encoding the fusion protein also falls within the scope of the present invention.

The ER retention signal may include the amino acid sequence KDEL (SEQ ID NO:2), preferably the ER retention signal is SEKDEL (SEQ ID NO:1). Inclusion of an ER retention signal in the fusion protein of the invention allows for endoplasmic reticulum retention of the expressed proteins. Other retention signals can also be used which, occur normally in animal and vegetable proteins localized in the ER for the construction of the cassette.

An advantage of a scFv of the present invention is the ease of expression, mutation and purification. These advantages arise, in part, from the ability to either stably or transiently express the scFv in a plant expression system. The use of a plant expression system facilitates purification of the scFv via standard protein purification techniques. However, the purification of the fusion proteins of the invention can be further simplified by adding one or more amino acid sequences that can ease purification of a scFv.

Typically, one sequence that can be added to a fusion protein of the invention in order to assist in its purification is a histidine tag, or "his tag". A histidine tag generally comprises a plurality of histidine residues. Passing the tagged protein over a column comprising a nickel N-(5-amino-1-carboxypentyl) iminodiacetic acid (Ni-NTA) agarose matrix can isolate fusion proteins comprising his tags.

The following example is offered by way of illustration and not by way of limitation.

Example 1

HRP-scFv Constructs and Infiltration

A construct encoding a chicken-derived immunoglobulin (IgY) single chain fragment variable (scFv) showing anti-rabbit IgG activity (B2) was tested and showed high binding activity to rabbit IgG protein. Another 2 constructs, B4 and F8, were also shown to have binding activity and were cloned and expressed, but purification and testing of functionality was only carried out with B2. The scFv genes were fused to a horseradish peroxidase (HRP) gene on their 5' terminus with a rigid α-helical linker (EAAAK)n (n=2) (SEQ ID NO:4) linker in between them. The HRP sequence included its native signal peptide responsible for targeting the protein to the endoplasmic reticulum (ER). Processing of HRP in the ER is essential for HRP activity. Two constructs for each scFv were made—one with a SEKDEL sequence (SEQ ID NO:1) for ER retention (HRP-scFv-SEKDEL) and one without (HRP-scFv).

A polyhistidine-tag (6×his-tag) (SEQ ID NO:5) was fused to the 3' termini of the fusion constructs to facilitate downstream purification. All expression constructs were cloned into the plant expression vector pTRAc. FIG. 1 shows a schematic of the constructs. Table 1 summarises the constructs which were made.

TABLE 1

| Constructs made of HRP-scFv fusions Construct |
| --- |
| pTRAc-HRP_B2his |
| pTRAc-HRP_B2SEKDELhis |
| pTRAc-HRP_B4his |
| pTRAc-HRP_B4SEKDELhis |
| pTRAc-HRP_F8his |
| pTRAc-HRP_F8SEKDELhis |

All recombinant constructs were confirmed through restriction digest, PCR and sequence analysis where relevant. All vectors were transformed into *Agrobacterium tumefaciens*.

*Nicotiana benthamiana* leaves were infiltrated with the recombinant *Agrobacterium* sp. and expression of HRP and the scFvs was verified individually by probing of western blots of crude leaf extracts with anti-chicken IgY or anti-6×his or anti-HRP antibodies.

Functionality of the expressed HRP-scFvs was tested and shown to bind to rabbit IgG—as determined by dotblots of rabbit IgG protein probed with scFv (crude leaf extracts) (FIG. 2) and alk-phos-labelled anti-chicken IgY and western blotting (data not shown).

In addition, preliminary qualitative functionality of the HRP component of the recombinant fusion proteins in the crude leaf extract preparations was established by the addition of HRP substrate to a droplet of plant extract. This resulted in a colorimetric result compared with the crude extract from the control plant which did not change colour (FIG. 3). It is very surprising that the plant-produced HRP-Ig is active as a secondary antibody in a very crude form (i.e. activity is detectable for western blotting when used as crude plant sap squeezed from a leaf).

It had been noted in the western blot results showing HRP_B2_SEKDEL expression however (data not shown) that there was a lot of 'free' HRP suggesting that there was some in vivo processing of the fusion protein being carried out. A check for signal peptides on the amino acid sequences of the HRP-scFvs showed that in all 3 cases there was a cleavage site adjacent to the start site of the scFv gene sequences which may have been the cause of excess 'free' HRP yields. In order to favour the production of fusion protein rather than free HRP, PCR and cloning was carried out to remove the signal sequences on all 3 scFv genes (B2, B4 and F8) and the HRP-scFv sequences reassembled, both including and excluding the SEKDEL sequence (SEQ ID NO:1) to yield 6 new constructs (Table 2).

TABLE 2

Figure 5:
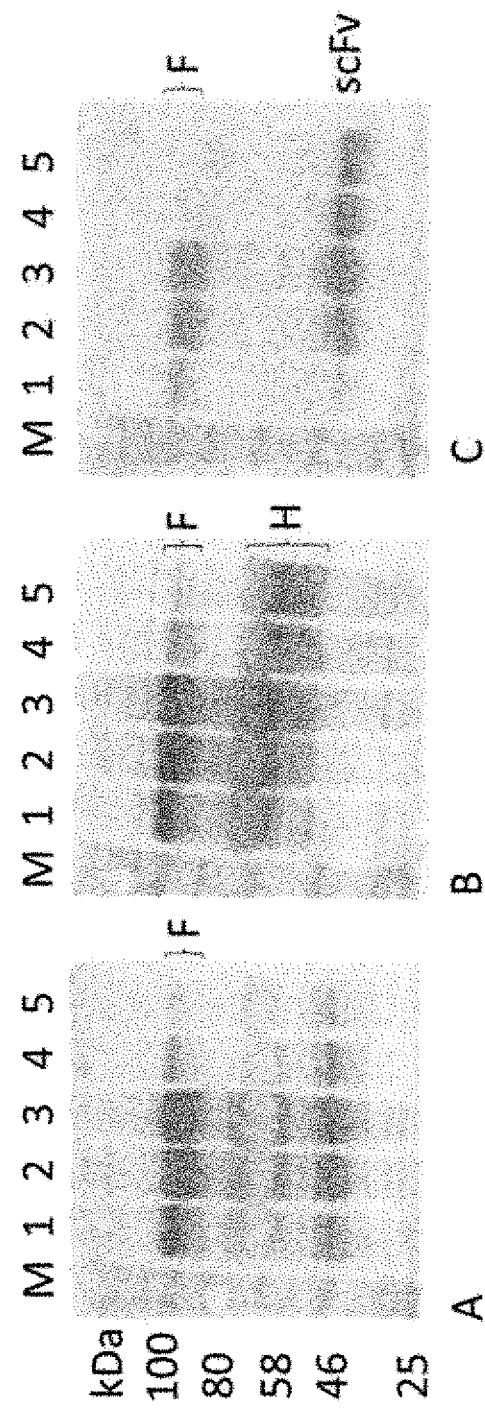
FIG. 5: Time trial studies of HRP-fused chicken-derived IgY scFv (HRP-B2_2his) expression in *N. benthamiana* using recombinant construct: pTRAc-HRP-B2_2his. The fusion protein was detected with either an anti-his (A), anti-HRP (B) or anti-chicken IgY (C) antibody. Plants were sampled 1 (lane 1), 2 (lane 2), 3 (lane 3), 5 (lane 4) and 7 (lane 5) days post-infiltration. Fusion proteins are indicated (F), along with HRP (H) and scFv.

Constructs re-made to exclude signal sequences of B2, B4 and F8
Construct pTRAc-HRP_B2_2his
pTRAc-HRP_B2_2SEKDELhis
pTRAc-HRP_B4_2his
pTRAc-HRP_B4_2SEKDELhis
pTRAc-HRP_F8_2his
pTRAc-HRP_F8_2SEKDELhis Infiltration using these constructs showed that the amount of recombinant fusion protein expressed compared to the previous constructs as visualised on western blots had increased, although there was still some 'free' HRP detected. FIG. 5 shows the fusion protein (F) encoded by the HRP_B2_2his construct lacking the ER retention signal.

As proof of concept a preliminary functionality test of the new HRP_B2_2 and HRP_B2_2SEKDEL fusion proteins was carried out by testing their ability to detect rabbit-bound antibodies (bound to several different antigens) on western blots.

Figure 6:
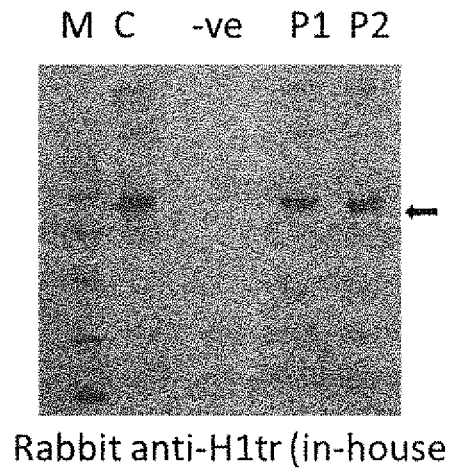
FIG. 6: Western blots of influenza H1tr, BFDV CP and GOx antigens probed with crude plant extract containing HRP_B2_2 scFvs. The plant-produced recombinant scFv was able to detect all 3 antigens when used as a secondary antibody.
Figure 6:
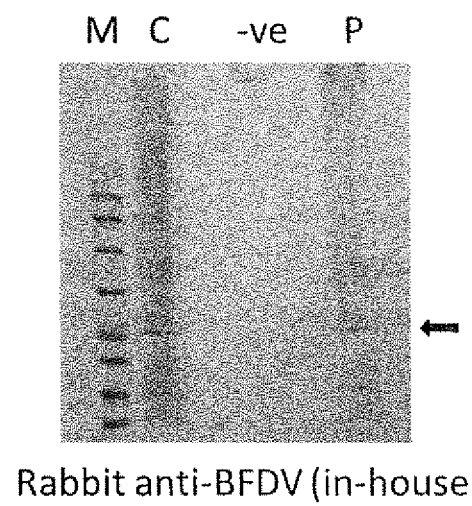

Glucose oxidase (GOx), influenza haemagglutinin (H1tr), beak and feather disease virus coat protein (BFDV CP) and influenza M1 were separated by SDS PAGE, transferred to nitrocellulose and probed with their respective rabbit antibodies. The blots were then probed with low dilutions of crude plant-produced HRP_B2_2 and HRP_B2_2SEKDEL. FIG. 6 shows the western blots probed with HRP_B2_2 scFvs. The recombinant secondary antibody was able to detect GOx (75 kDa), H1tr (70 kDa) and BFDV CP (27 kDa).

Analysis showed that both the ER-retained fusion protein of B2 (HRP_B2_2SEKDEL) as well as the one lacking the ER retention signal of B2 (HRP_B2_2) expressed equally well and therefore both constructs were continued with for the development of a purification protocol.

Purification

Figure 7:
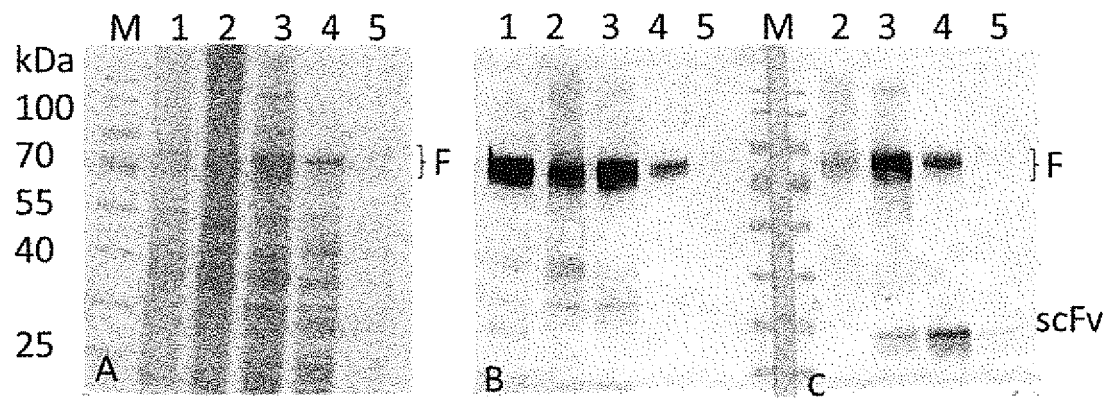
FIG. 7: Ammonium sulphate fractionation of total soluble protein extracted from HRP_B2_2SEKDELhis-expressing *N. benthamiana*. Lanes: Prestained protein ladder (M); total soluble protein extract from leaf tissue (1); 0-40% fraction (2); 40-60% fraction (3); 60-80% fraction (4); 80-90% fraction (5). (A) Coomassie Blue staining along with western blot analysis using either anti-his antibody (B) or anti-chicken IgY antibody, shows enrichment of HRP_B2_2SEKDELhis (F) in the 40-60% fraction, while showing accumulation of free scFv in the 60-80% fraction.

As a first step towards purifying the recombinant fusion protein, ammonium sulphate fractionation of HRP_B2_2SEKDELhis extracted from leaf tissue three days post-infiltration (used as a test batch) was investigated. Fractionation showed that the majority of HRP_B2_2SEKDELhis could be found in the 40-60% fraction (FIG. 7), while there was a small amount present in the 60-80% as well as the 0-40% fraction. The 40-60% fraction was further purified using nickel affinity chromatography.

Figure 8:
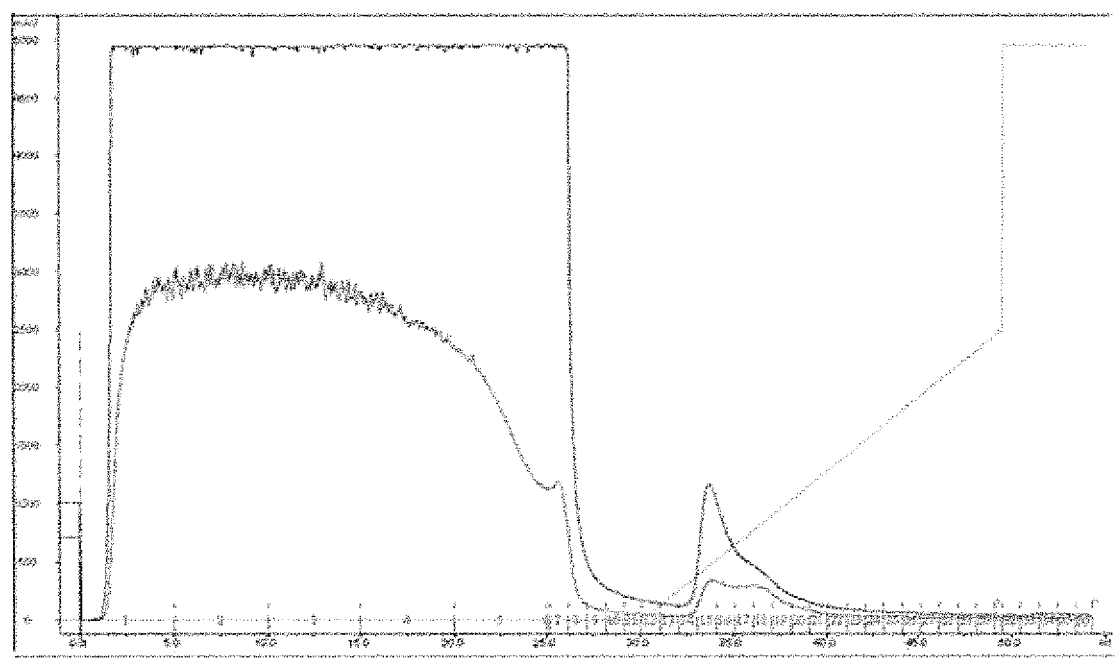
FIG. 8: Purification profile of HRP-B2_2_SEKDEL protein on a HisTrap affinity chromatography column.

The purification protocol for both HRP_B2_2 and HRP_B2_2SEKDEL was developed making use of a His-Trap column (GE Lifesciences) operated by a fast protein liquid chromatography (FPLC) system (ÄKTAexplorer 100). After much trial and error, a purification protocol was established that produced relatively pure protein eluted using 10 mM imidazole. FIG. 8 shows the elution profile of HRP_B2_2SEKDEL with a protein absorbance peak spanning fractions 15 to 19.

Figure 9:
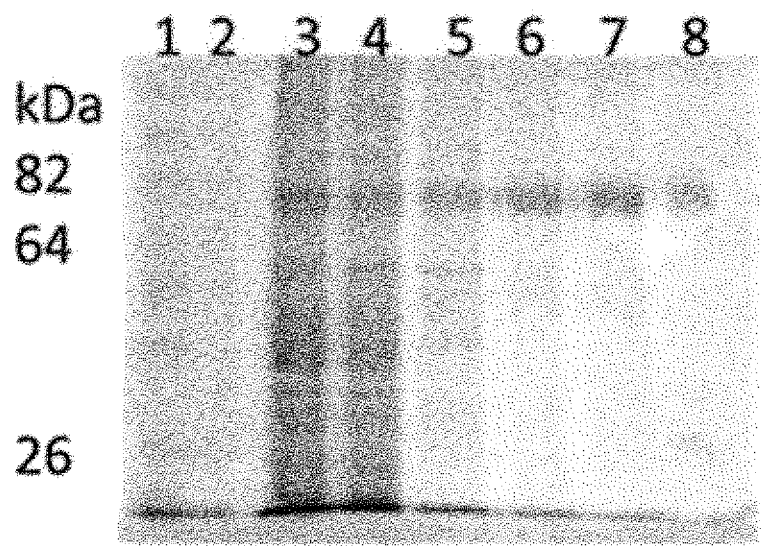
FIG. 9: SDS-PAGE of Coomassie-stained HRP_B2_2_SEKDEL fractions purified by 6×his affinity chromatography.
Figure 10:
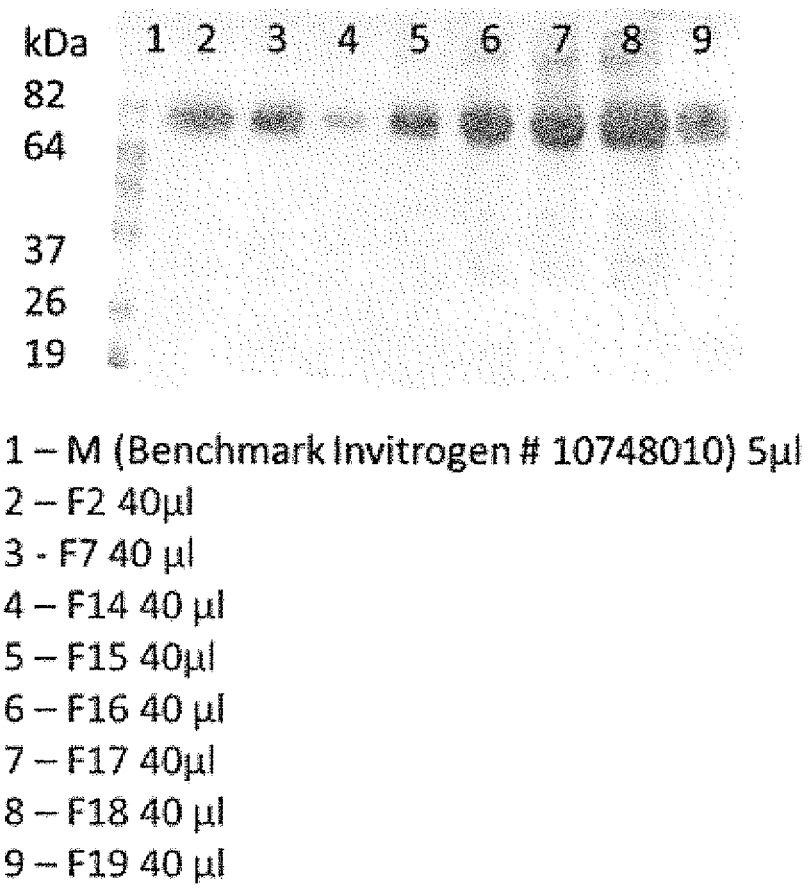
FIG. 10: Western blot of HRP_B2_2_SEKDEL fractions purified by affinity chromatography using anti-6×his antibody (1:1000).

Fractions 2, 16, 17, 18 and 19 were separated by SDS-PAGE and stained with Coomassie blue (FIG. 9) while fractions 2, 7 and 14-19 were separated by SDS-PAGE and blotted onto nitrocellulose and probed with anti-6×his antibody (FIG. 10).

The Coomassie-stained gel showed good purification of the protein, particularly in fractions 17 to 19 (lanes 6 to 8).

The western blot verified that the bands visualised by Coomassie blue staining in FIG. 9 were that of the recombinant fusion protein. The highest concentrations of protein appeared to be in fractions 17 and 18. These 2 fractions were subsequently pooled and dialysed into potassium phosphate buffer in order to determine the HRP activity and test the functionality of the recombinant fusion protein in ELISA and on a western blot.

HRP Activity Testing and Immunoassay Testing

An HRP assay was carried out on the purified pooled sample and shown to be active albeit quite low with a specific activity of 0.214 U/ml protein. Previous activity measurements of recombinant HRP on its own have ranged from 9 to 750 U/ml. The concentration of protein was measured by Bradford assay to be 1.37 mg/ml.

Figure 11:
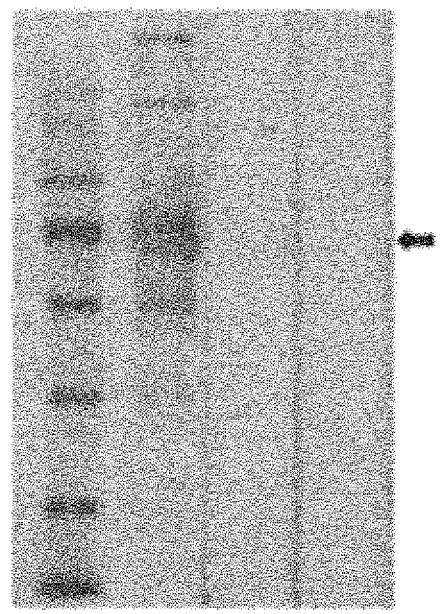
FIG. 11: Western blot of GOx protein probed with commercial anti-rabbit-HRP (C) and plant produced HRP-IgG (P) secondary antibodies.

The activity of the purified recombinant fusion protein was tested using only GOx antigen in western blotting. The HRP_B2_2SEKDEL scFv was able to detect rabbit anti-GOx antibody when used at a 1:100 dilution (FIG. 11) which is very promising.

Figure 12:
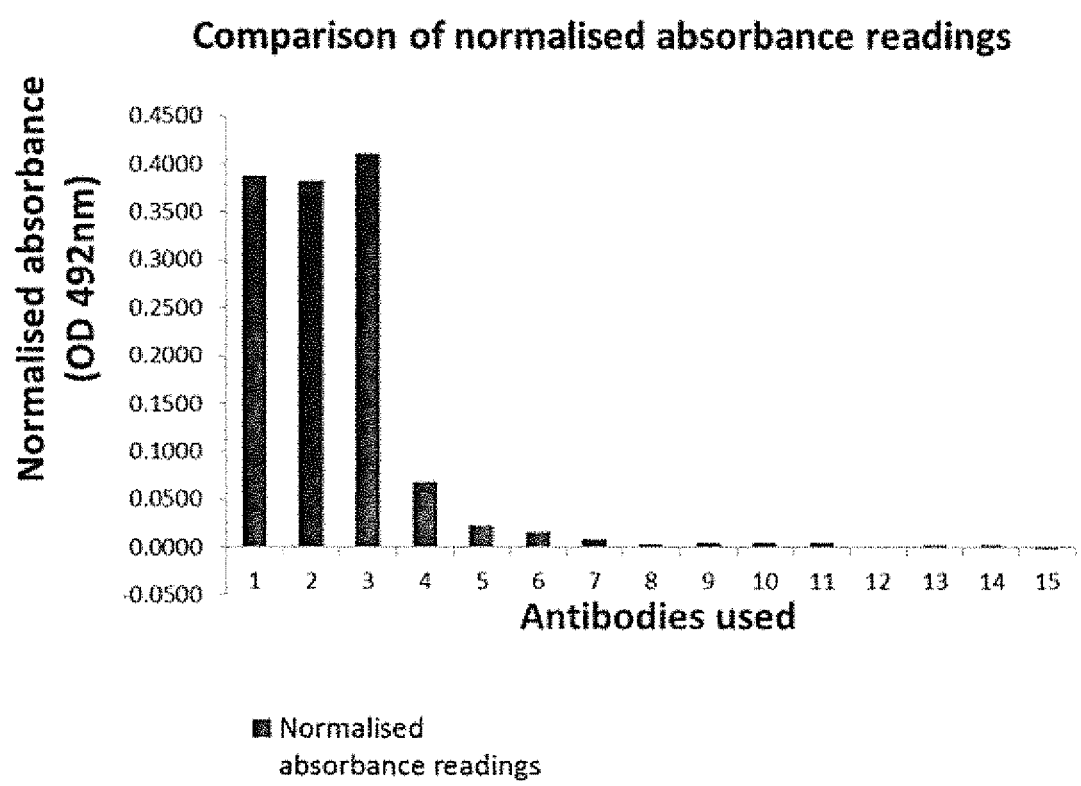
FIG. 12: Graphical illustration of ELISA absorbance readings. Antibodies 1 to 3 represent detection using the commercially available polyclonal anti-rabbit IgG/HRP (refer to Table 2.3 for dilutions) and lanes 4 to 15 represent detection using the plant-produced secondary HRP-scFv.

The purified HRP fusion protein was further tested for functionality in an ELISA using GOx as the binding antigen. Table 3 shows the absorbance values of the different secondary antibody dilutions tested. Compared with the commercially available polyclonal swine anti-rabbit IgG/HRP, the detecting signal was fairly low (FIG. 12). However, binding of the plant-produced HRP-scFv occurred when a 1:100 dilution was used indicating that the recombinant protein is functional. It is possible that the signal was quite low because the activity of the HRP was low.

TABLE 3

Absorbances of ELISA after detection using varying commercial secondary antibody dilutions (Anti-GOx swine) or plant-produced secondary HRP-scFv (Anti-GOx scFv).

| | | Avg Abs OD 492 | normalised |
|---|---|---|---|
| 1 | AntiGox 1/10000 Swine | 0.4270 | 0.3867 |
| 2 | AntiGox 1/20000 Swine | 0.4217 | 0.3813 |
| 3 | AntiGox 1/30000 Swine | 0.4507 | 0.4103 |
| 4 | AntiGox 1/10000 scFv 1/100 | 0.1087 | 0.0683 |
| 5 | AntiGox 1/20000 scFv 1/100 | 0.0627 | 0.0223 |
| 6 | AntiGox 1/30000 scFv 1/100 | 0.0553 | 0.0150 |
| 7 | AntiGox 1/10000 scFv 1/1000 | 0.0477 | 0.0073 |
| 8 | AntiGox 1/20000 scFv 1/1000 | 0.0427 | 0.0023 |
| 9 | AntiGox 1/30000 scFv 1/1000 | 0.0440 | 0.0037 |
| 10 | AntiGox 1/10000 scFv 1/2000 | 0.0440 | 0.0037 |

TABLE 3-continued

Absorbances of ELISA after detection using varying commercial secondary antibody dilutions (Anti-GOx swine) or plant-produced secondary HRP-scFv (Anti-GOx scFv).

| | | Avg Abs OD 492 | normalised |
|---|---|---|---|
| 11 | AntiGox 1/20000 scFv 1/2000 | 0.0440 | 0.0037 |
| 12 | AntiGox 1/30000 scFv 1/2000 | 0.0403 | 0.0000 |
| 13 | AntiGox 1/10000 scFv 1/5000 | 0.0407 | 0.0003 |
| 14 | AntiGox 1/20000 scFv 1/5000 | 0.0413 | 0.0010 |
| 15 | AntiGox 1/3000 scFv 1/5000 | 0.0393 | −0.0010 |
| | Blank | 0.0403 | |

Example 2

Stability and Activity of scFv-HRP in Different Buffers

The small-scale purification of scFv-HRP in Example 1 was carried out using $NaPO_4$ pH 7.0 buffer. It was decided to investigate which buffers were the most suitable for retaining HRP activity. A brief look at the stability of the purified, concentration scFv-HRP in four additional buffers was also undertaken (Table 4). Pre-purified scFv-HRP samples (100 µl) were dialysed into several different buffers as shown in Table 4.

TABLE 4

Different buffers tested

| Buffer | Concentration | pH |
|---|---|---|
| Tris | 0.1M | 8 |
| Carbonate | 0.1M | 10 |
| Formate | 0.1M | 3 |
| Sodium Phosphate | 0.1M | 7 |
| 1XPBS | 0.1M | 7.6 |

Figure 13:
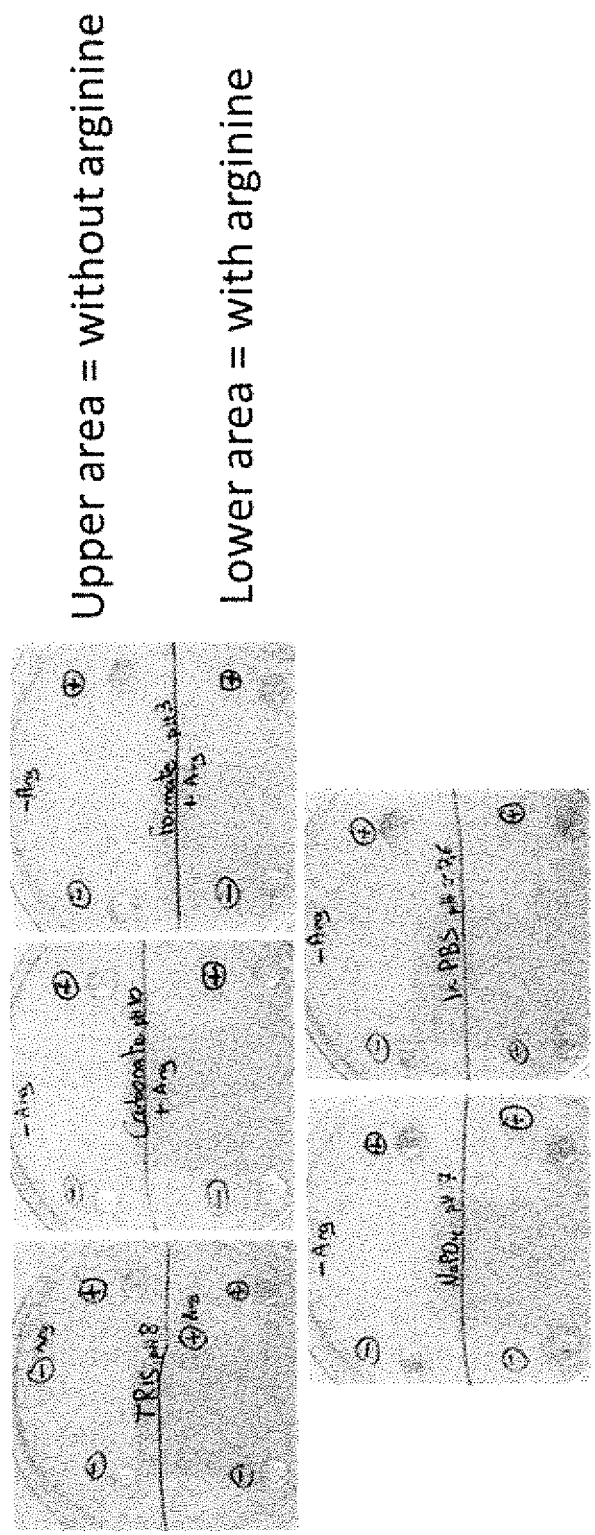
FIG. 13: A) HRP activity tested in a range of buffers with and without L-arginine. Left side of plate=negative control (−); right side of plate=test sample (+). B) HRP activity of crude extract in different buffers; +=L-Arginine added; −=no L-Arginine added.
Figure 13:
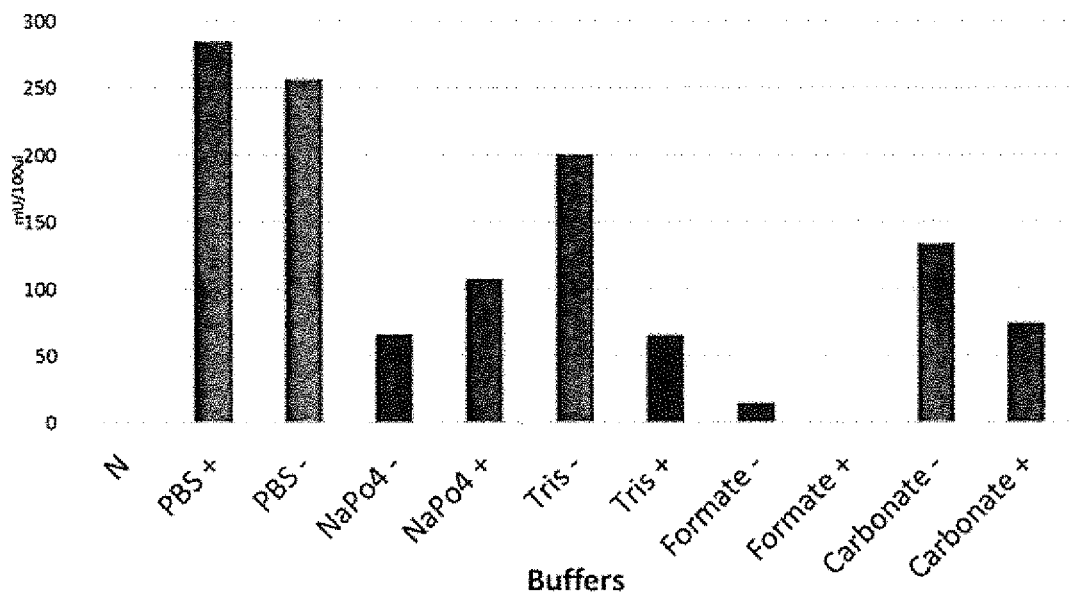

All of the above buffers were tested both inclusive and exclusive of L-Arginine. After two hours of dialysis at 4° C. the samples were tested for HRP activity using TMB peroxidase substrate (KPL). As seen in FIG. 13, 1×PBS pH 7.6 and $NaPO_4$ pH 7.0 resulted in the most significant colorimetric reaction which indicates a higher HRP activity (FIG. 13A). However, HRP activity as measured by the guaiacol assay shows that 1×PBS gave the highest activity (FIG. 13B) and this buffer was therefore continued with for scFv-HRP scaled up extraction and purification.

Two scaled up purifications (purification 1 and purification 2) as detailed in Examples 3 and 4 were carried out on leaves infiltrated with pTRAc-HRP_B2_2SEKDEL to determine the feasibility of pilot scale production of the plant-produced scFv-HRP.

Example 3

Large Scale Purification 1

Figure 14:
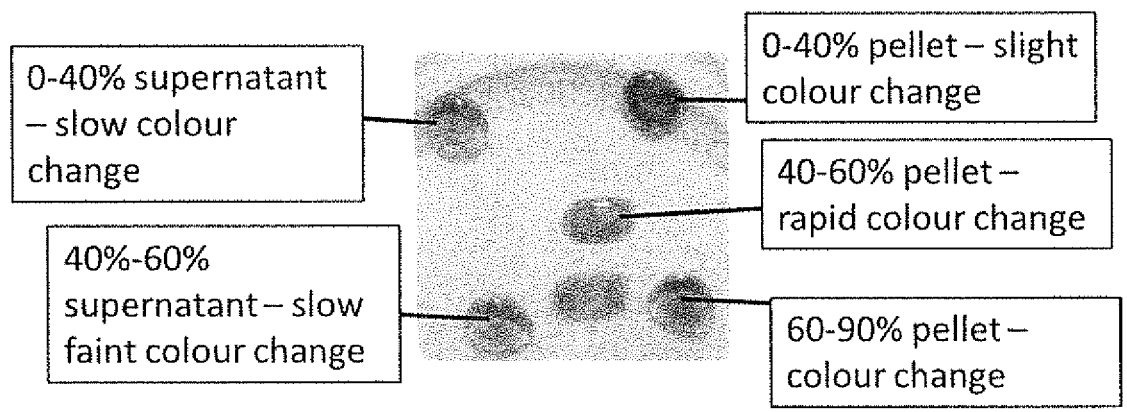
FIG. 14: Ammonium sulphate fractions tested for HRP activity using TMB peroxidase substrate.

For purification 1, 64 plants were infiltrated with recombinant *Agrobacterium* harbouring pTRAc-HRP_B2_2SEKDEL at a culture OD of 0.25. Three hundred grams of infiltrated *N. benthamiana* leaves were cut up and homogenised in 1×PBS buffer (pH 7) at a ratio of 1:3 (mass:volume). The extract was filtered through three layers of Miracloth and then centrifuged twice at 10 000 g for 10 min to get rid of any remaining particulate matter. The supernatant was subjected to a 0-40% ammonium sulphate precipitation step for 2 hours with agitation at 4° C., after which it was centrifuged for 10 minutes at 10 000 g to pellet the precipitated proteins. The supernatant was subjected to a second overnight 40-60% ammonium sulphate precipitation step and centrifuged again for 10 min at 10 000 g. A 60-90% fractionation was carried out on the resulting supernatant. The pellet was then resuspended in 1×PBS. Samples from these procedures were tested with TMB peroxidase substrate to preliminarily determine HRP activity (FIG. 14).

The scFv-HRP sample was purified using a batch purification method. The supernatant was bound to 1.5 ml nickel charged resin overnight at 4° C. and then for 2 hours at room temperature. Batch purification was performed with 10 column volume washes of 5 mM imidazole containing PBS and 10 column volume washes of 20 mM imidazole containing PBS. Final elution from nickel charged resin was performed with 120 mM imidazole containing PBS.

Figure 15:
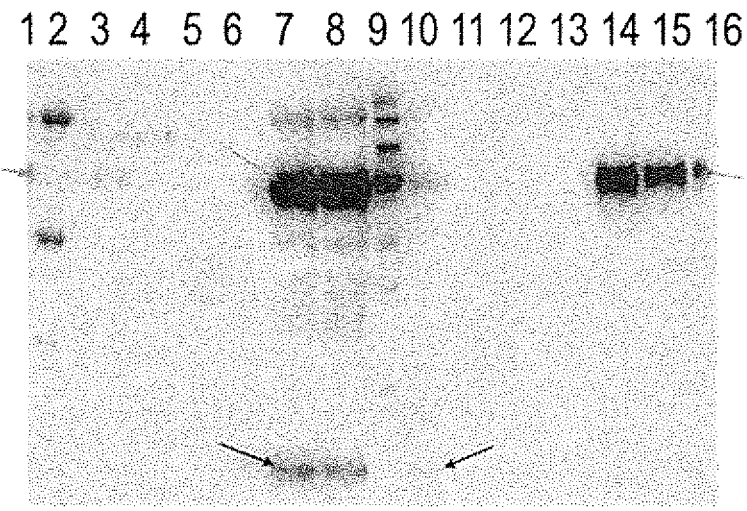
FIG. 15: Analysis of scFv-HRP fractions from ammonium sulphate, dialysis and purification. Western blot probed with (A) anti-his primary conjugate 1:2000 and (B) stain-free SDS gel. scFv-HRP fusion protein and free scFv are clearly detectable. Lanes 14-16 show the presence of the partially purified scFv-HRP after 40-60% ammonium sulphate fractionation.
Figure 15:
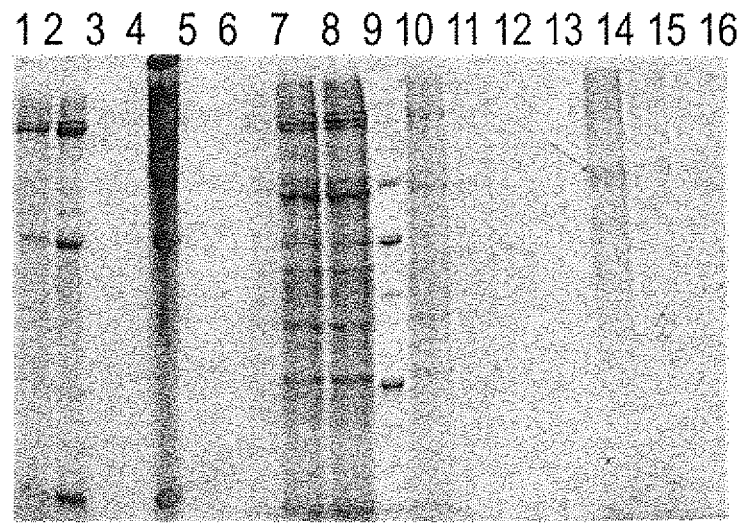

Fractions were collected and protein concentrations measured using the Bradford assay with a BSA standard curve. Samples were also treated with loading buffer and separated by PAGE on a 10% acrylamide gel. One gel was blotted onto nitrocellulose which was washed with blocking buffer (PBS 10×, 5% fat free milk, 1% Tween 20) and probed with anti-polyhistidine antibody diluted 1:2000 in blocking buffer. The gel was incubated overnight, washed 3× for 15 min with blocking buffer and then probed with secondary alkaline phosphatase-conjugated anti-mouse antibody diluted 1:10000 (FIG. 15A). After blotting onto nitrocellulose, the polyacrylamide gel was viewed in order to detect protein (FIG. 15B). The three partially purified scFv-HRP eluted fractions after 40-60% ammonium sulphate fractionation were pooled and then subjected to a concentration step.

Concentration of Purified scFv-HRP

Figure 16:
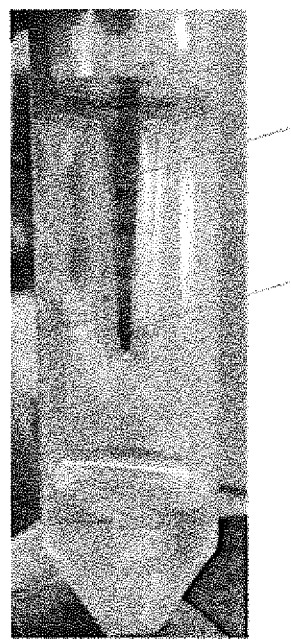
FIG. 16: Concentration of the DE sample into the different layers using an Amicon filtration unit.
Figure 17:
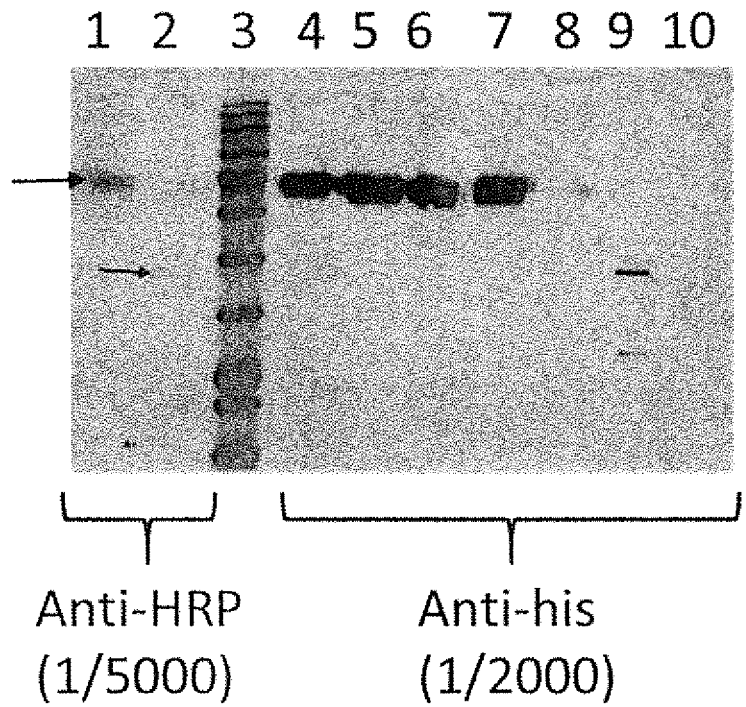
FIG. 17: Western blot showing the presence of the scFv-HRP protein and free HRP.

Fifteen ml of the dialysed eluate (DE) was then concentrated to 1.2 ml using an Amicon filter tube with a 3000 MW cut off point. This was done by centrifugation at 4000 rpm for 37 min. At this point two layers were visualised in the tube, a lighter upper layer (DEcs—supernatant) and a darker lower layer (DEcp—pellet) (FIG. 16). These were removed and kept separate. Samples were run on a 10% polyacrylamide gel (FIG. 17). Some of the DE scFv-HRP was lyophilised (1 ml) to determine whether the protein would remain stable and active during this process as well as after re-constitution. The lyophilised protein was subsequently reconstituted in 100 µl of 1×PBS+L-Arginine (0.1) and tested for HRP activity. Samples of the lyophilised protein were run on a 10% polyacrylamide gel (lane 4 of FIG. 17).

Functionality Test of scFv-HRP

Figure 18:
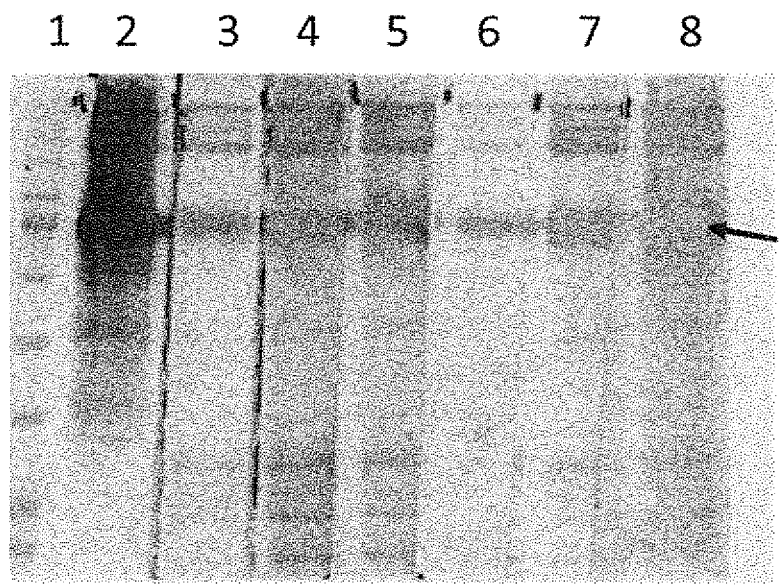
FIG. 18: Western blot of plant made glucose oxidase (GOx). Primary rabbit anti-GOx (1:2000) was used and different fractions and dilutions of the scFv-HRP fusion were used as the secondary probe. The arrow indicates GOx.

The functionality of the differently-treated purified scFv-HRP samples was tested for its ability to bind to and detect rabbit anti-GOX antibodies on a western blot, comparing it to the commercially available HRP-conjugated rabbit antibody (FIG. 18—lane 2). All versions of the protein (lyophilised and both concentrated versions) were successful in detecting the antibodies in all states tested.

The functionality of plant-produced scFv-HRP (DE sample) was tested on a further 6 rabbit antibodies by western blotting. Results are summarised in Table 5. From a total of 7, three of the rabbit antibodies were recognised by the scFv-HRP.

TABLE 5

Plant produced scFv-HRP tested on a western blot
to detect a range of rabbit antibodies.

| Detected | Antigen name | Primary | Secondary |
|---|---|---|---|
| No | M2e (30 µl) | Rb pAb to Influenza A virus M2. (1/1000) | Anti-Rabbit scFv-HRP plant made. (1/1000) DE-label |
| No | HA (30 µl) | Rb pAb to HA1 (H1N1) A/California/14/2009. (1/1000) | Anti-Rabbit scFv-HRP plant made. (1/1000) DE-label |
| Yes | Plant GOx (30 µl) | Rb anti-GOx. (1/2000) | Anti-Rabbit scFv-HRP plant made. (1/1000) DE-label |
| Yes | H1tr 07/08/14 plant (30 µl) | Rab2 anti-H1tr 6/10. (1/2000) | Anti-Rabbit scFv-HRP plant made. (1/1000) DE-label |
| Yes | BFDV incl. bad 7/10 plant. (30 µl) | Rb 40h Pos serum. (1/1000) | Anti-Rabbit scFv-HRP plant made. (1/1000) DE-label |
| No | LO.L1 17.07. (30 µl) | Gardasil. (1/2000) | Anti-Rabbit scFv-HRP plant made. (1/1000) DE-label |
| No | L2 plant protein (30 µl) | Anti-L2 D42 Rb serum. (1/1000) | Anti-Rabbit scFv-HRP plant made. (1/1000) DE-label |

Activity Test of HRP (Guaiacol Assay)

The HRP activity of the DE sample of scFv-HRP was measured using the guaiacol assay. It was calculated to be 27042 mU per ml. The protein concentration was measured to be 0.7 mg/ml and therefore the specific activity of the HRP was calculated to be 27042 U/0.7 mg=38631 U/mg.

Example 4

Large Scale Purification 2

Figure 19:
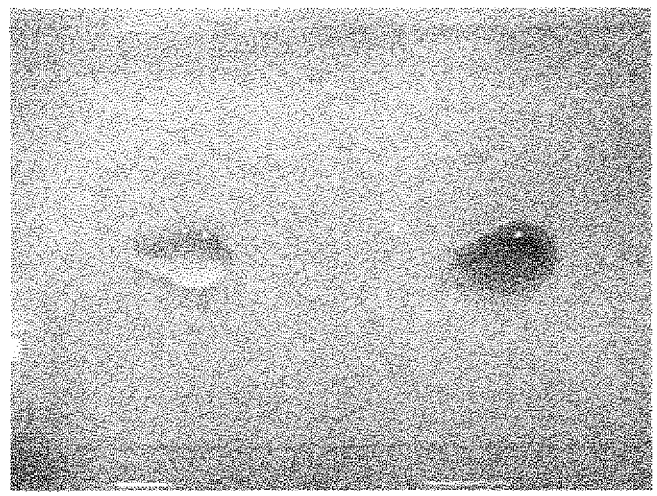
FIG. 19: Activity analysis of the supernatant sample (right hand side) prior to ammonium sulphate precipitation, using the Ultra TMB-ELISA substrate. 1×PBS buffer was used as a negative control (left hand side).

The second purification involved the infiltration of 40 *N. benthamiana* plants as described in Example 3. Plant leaf material (264 g) was shredded into smaller pieces and 1×PBS buffer added in a 3:1 ratio (buffer:plant mass). The plant mass was homogenized in 1×PBS using a hand-held blender. The homogenized material was filtered through three layers of Mira-cloth and the filtrate was centrifuged twice at 8 000 g in a JA14 Beckman rotor for 15 minutes to remove any remaining plant leaf debris. The supernatant was preliminarily tested to determine that HRP activity was present in the sample prior to ammonium sulphate precipitation (FIG. 19).

The supernatant volume was recorded (800 ml) and the amount of ammonium sulphate required for a 0-35% precipitation was calculated. Ammonium sulphate was added a spoonful at a time to the supernatant and precipitation was carried out overnight at 4° C. The solution was centrifuged at 14 000 g for 20 minutes and the supernatant was retained for a 35-75% ammonium sulphate precipitation. Again, ammonium sulphate was added a spoonful at a time to the supernatant and precipitation was carried out overnight at 4° C. Following centrifugation at 14 000 g for 20 minutes, the 2 pellets were stored at −20° C.

The following day, one pellet was subjected to nickel affinity column purification using a HisTrap FF affinity column operated by an Äkta Explorer and the other half was subjected to batch binding as described for purification.

Figure 20:
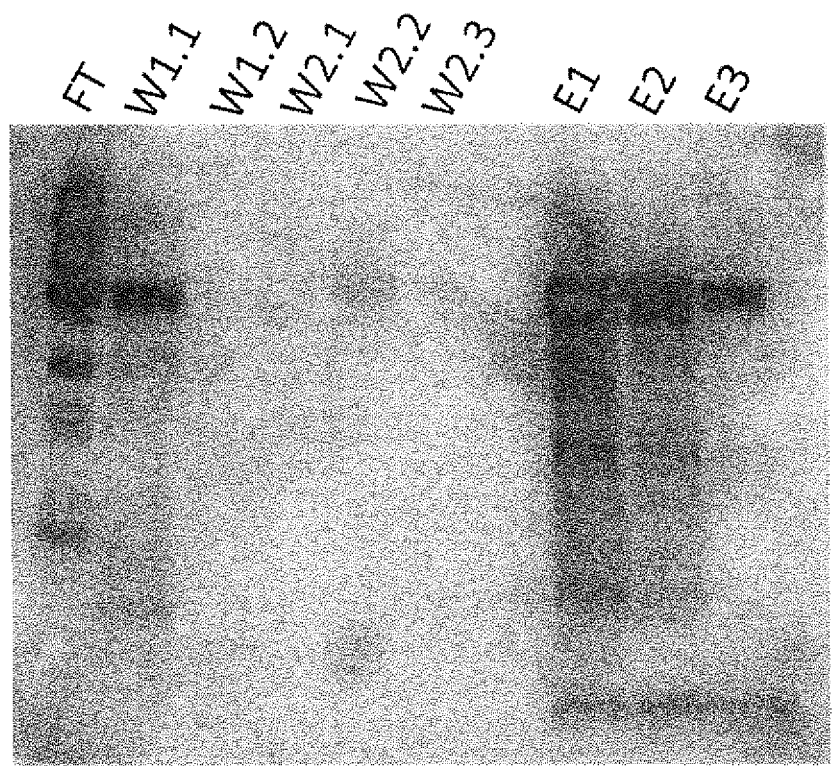
FIG. 20: Western blot with Anti-his probe for the batch binding purification. FT=column flow through, W1.1=50 ml wash 1, W1.2=50 ml wash 1, W2.1-2.3=50 ml wash 2, 3-fold. E1=Eluted fraction 1, E2=Eluted fraction 2, E3=Eluted fraction 3.

For batch purification, one pellet was removed from the freezer for the first purification using a batch purification protocol as follows: The pellet was re-suspended in 100 ml of 1×PBS containing 5 mM imidazole, and subjected to centrifugation for 45 mins at 14 000 g. The supernatant was bound to 1.5 ml nickel charged resin overnight at 4 and then for 2 hours at room temperature. Batch purification was performed with 100 column volume washes of 5 mM imidazole containing PBS, 100 column volume washes of 20 mM imidazole containing PBS. Final elution from nickel charged resin was performed with 120 mM imidazole containing PBS. Fractions from the batch purification were collected and analyzed via anti-his western blot (FIG. 20).

Figure 21:
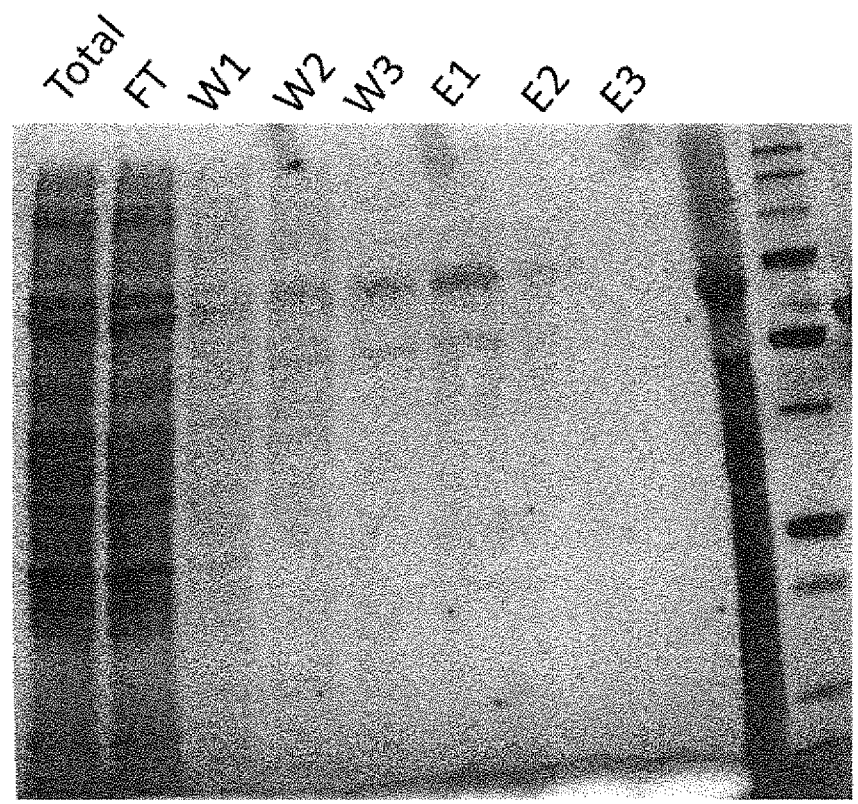
FIG. 21: SDS-PAGE of the AKTA purification. Total=Total protein, FT=column flow through, W1=Wash 1, W2=Wash 2, W3=Wash 3, E1=Eluted fraction 1, E2=Eluted fraction 2, E3=Eluted fraction 3. Last lane is the protein molecular mass marker.
Figure 22:
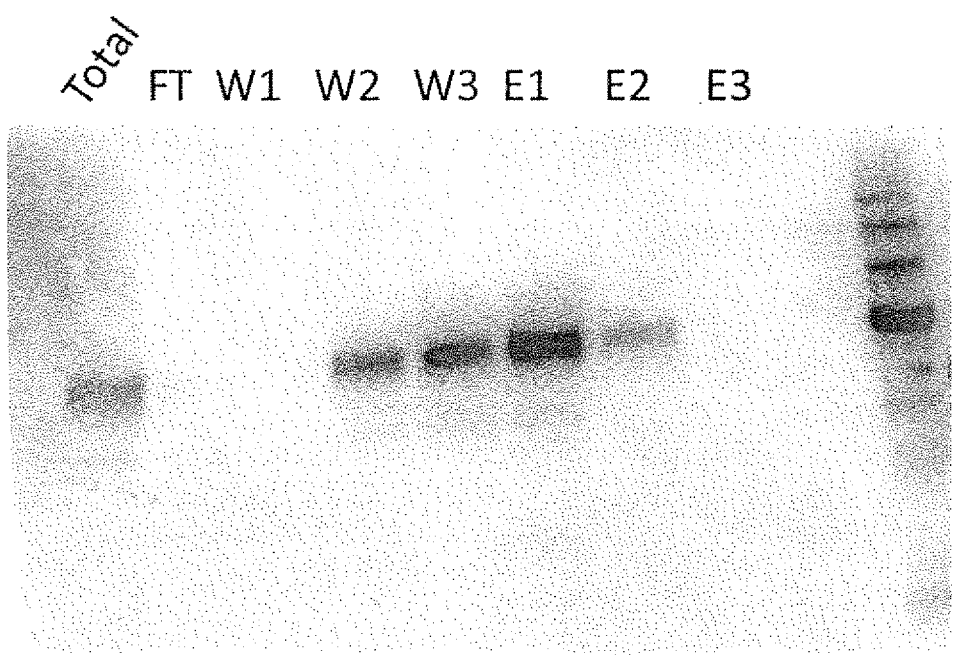
FIG. 22: Western blot with Anti-His probe of the AKTA purification. Total=Total protein, FT=column flow through, W1=Wash 1, W2=Wash 2, W3=Wash 3, E1=Eluted fraction 1, E2=Eluted fraction 2, E3=Eluted fraction 3. Last lane is the protein molecular mass marker.

For column purification, a pellet was removed from the freezer for the first purification using a the AKTA protocol as follows: The pellet was re-suspended in 100 ml of 1×PBS containing 5 mM imidazole, and subjected to centrifugation for 45 mins at 14 000 g. The supernatant was bound to a 1 ml nickel charged column at 1 ml per minute. Purification was performed at 2 ml per minute with 15 column volume washes of 5 mM imidazole containing PBS, 15 column volume washes of 15 mM imidazole containing PBS and 15 column volume washes of 35 mM imidazole containing PBS. Final elution from the column was performed with 120 mM imidazole containing PBS. Fractions from the column purification were collected and analyzed via SDS-PAGE (FIG. 21) and anti-his western blot (FIG. 22).

Eluted fractions containing the protein of interest were pooled and dialyzed three times against PBS buffer at 4° C. and filtered through a 0.45 µM filter.

Activity Test of HRP (Guaiacol Assay)

A guaiacol assay was performed on all the scFv-HRP purified (Purification 1; Purification 2—batch purification; and Purification 2—column purification).

Protein concentrations of the samples in this Example were measured to be 0.5 mg/ml. The column-purified (AKTA) sample was calculated to have an activity of 29507 mU per ml. Therefore the specific activity of the HRP was calculated to be 59014 mU/mg. Batch-purified HRP (Example 4) activity was calculated to be 17857 mU per ml and therefore the specific activity of the HRP was 35714 mU/mg. The results are summarised in Table 6 below.

TABLE 6

Summary of HRP specific activity of three
different batches of purified scFv-HRP.

| Batch | Protein concentration (mg/ml) | HRP activity (mU/ml) | Calculated specificity (mU/mg) |
|---|---|---|---|
| Purification 1 | 0.7 mg/ml | 27042 | 38631 |
| Purification 2-column (AKTA) | 0.5 mg/ml | 29507 | 59014 |
| Purification 2-batch | 0.5 mg/ml | 17857 | 35714 |

Functionality of scFv-HRP

Binding/functionality of the purified proteins was tested using dot blots rather than western blotting due to time constraints.

Figure 23:
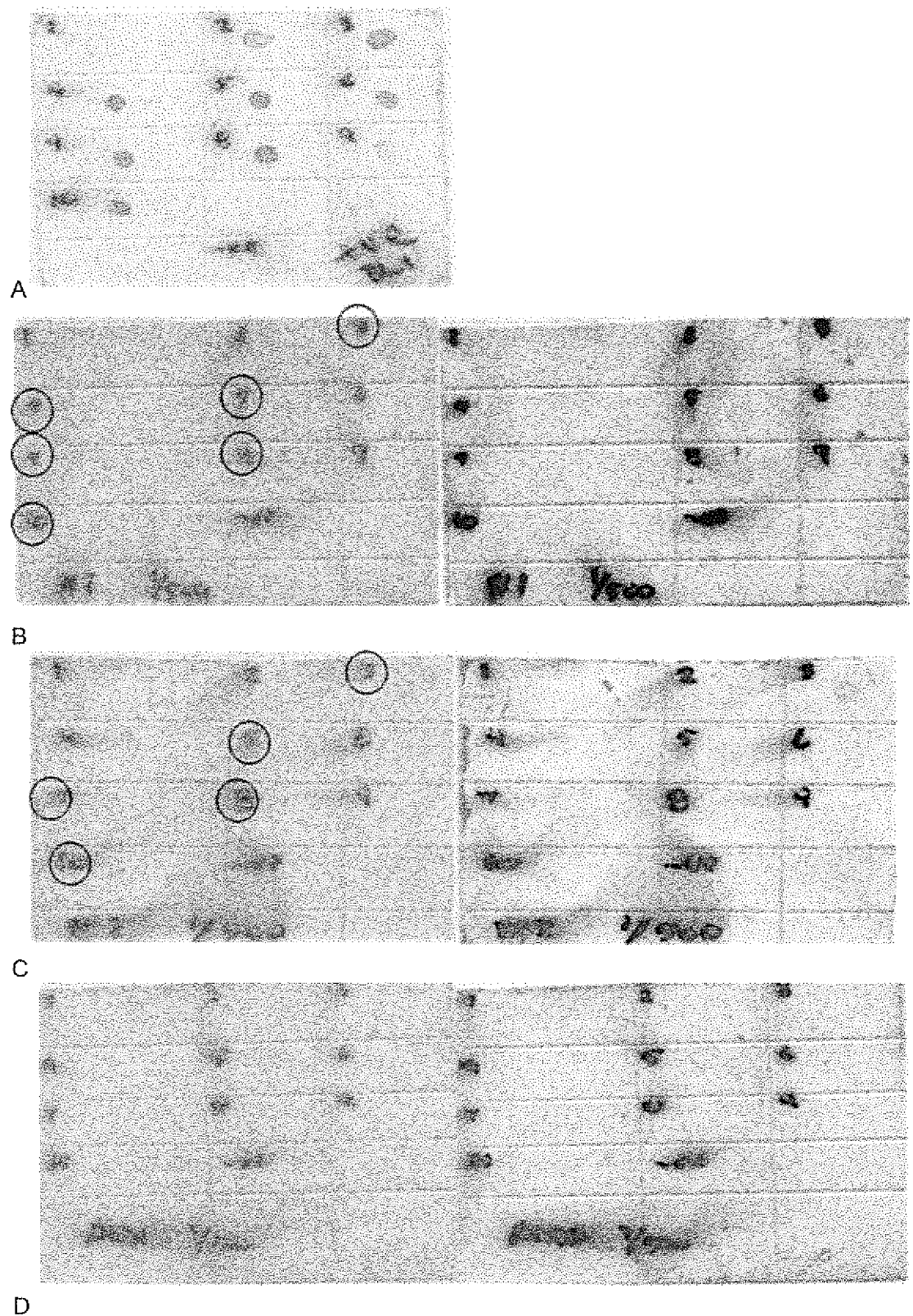
FIG. 23: (A) Positive control blot probed with Polyclonal Swine Anti-Rabbit Immunoglobulins/HRP (1/4000). (B) Blot probed with scFv-HRP from purification 1. (C) Blot probed with scFv-HRP from purification 2 (batch-purified). (D) Blot probed with scFv-HRP from purification 2 (column-purified). The numbers on the blots represent the different rabbit primary antibodies used. Circles indicate the dots which had a positive reaction.

The different primary rabbit antibodies were dotted onto nitrocellulose membrane (2 µl of 1/500 dilution in 1×PBS) for each antibody and allowed to dry. The nitrocellulose was blocked in blocking buffer (as described for western blotting in Example 3). The blots were then probed with 1:500 diluted scFv-HRP (for each of the batches from Example 3; Example 4—batch purification; and Example 4—column purification). The blots were washed and then developed with BM blue POD substrate. The positive control turned purple immediately. However the other dots only had a slight increase in colour change. Results are shown in FIG. 23.

A summary table of results can also be seen below (Table 7). The + symbols in the table give an indication of the intensity of the coloured dot that was visualised (i.e. + very low signal and ++++ very high signal).

TABLE 7

Testing anti-rabbit scFv-HRP as secondary against a range of rabbit primary antibodies.

| | | | Signal detected on dot blot indicating anti-rabbit scFv-HRP binding to primary rabbit antibody | | | |
|---|---|---|---|---|---|---|
| | | | | 1st Batch | 2nd Batch | |
| Dots | Antigen | Primary | Positive control | Batch binding purification | Batch binding purification | AKTA purification |
| 1 | M2e (30 µl) | Rb pAb to Influenza A virus M2. (1/500) | No | No | No | No |
| 2 | HA (30 µl) | Rb pAb to HA1 (H1N1) A/California/14/2009. (1/500) | Yes +++ | No | No | No |
| 3 | Plant GOx (30 µl) | Rb anti-GOx. (1/500) | Yes ++++ | Yes ++ | Yes ++ | No |
| 4 | H1tr 07/08/14 plant (30 µl) | Rab2 anti-H1tr 6/10. (1/500) | Yes ++++ | Yes + | No | No |
| 5 | BFDV incl. bad 7/10 plant. (30 µl) | Rb 40h Pos serum. (1/500) | Yes ++++ | Yes ++ | Yes + | No |
| 6 | LO.L1 17.07. (30 µl) | Gardasil. (1/500) | Yes ++++ | No | No | No |
| 7 | L2 plant protein (30 µl) | Anti-L2 D42 Rb serum. (1/500) | Yes ++++ | Yes + | Yes + | No |
| 8 | M1 | Rb serum anti-M1 #2 (968) (Francisco) (1/500) | Yes ++++ | Yes ++ | Yes + | No |
| 9 | GFP | Rb anti-GFP (20/4/16) (1/500) | Yes ++ | No | No | No |
| 10 | ZEUS | Rb-Zeus IgG (21/4/87) (1/500) | Yes ++++ | Yes ++ | Yes + | No |
| −ve | His tag | Mouse anti-his (1/500) | No | No | No | No |

The invention claimed is:

1. A method for producing a fusion protein in a plant cell, the fusion protein having the formula:

$$X_1\text{-}X_2\text{-}X_3\text{-}(X_4)_n\text{-}X_5 \quad (I)$$

alternatively, a fusion protein having the formula:

$$X_3\text{-}X_2\text{-}X_1\text{-}(X_4)_n\text{-}X_5 \quad (II)$$

wherein $X_1$ is a horseradish peroxidase polypeptide, $X_2$ is a peptide linker, $X_3$ is an scFv, $X_4$ is an endoplasmic reticulum retention signal, $X_5$ is a histidine tag and n is 0 or 1, the method comprising:
transforming the plant cell with an expression vector comprising a nucleic acid molecule encoding the fusion protein,
expressing the fusion protein in the plant cell, and
recovering the fusion protein from the plant cell.

2. The method of claim 1, wherein the plant cell is a *Nicotiana* sp. plant cell.

3. The method of claim 1, wherein the scFv has immunoglobulin binding activity.

4. The method of claim 3, wherein the immunoglobulin binding activity is selected from the group consisting of anti-mouse, anti-donkey, anti-rabbit, anti-horse, anti-human, anti-chicken, anti-goat, and/or anti-sheep binding activity.

5. The method of claim 4, wherein the immunoglobulin binding activity is anti-rabbit immunoglobulin binding activity.

6. The method of claim 1, wherein n is 1.

7. The method of claim 1, wherein the endoplasmic reticulum retention signal is selected from the group consisting of HDEL (SEQ ID NO:3), KDEL (SEQ ID NO:2), and SEKDEL (SEQ ID NO:1).

8. The method of claim 1, wherein the histidine tag is a 6× histidine tag.

9. The method of claim 1 wherein the fusion protein further includes a human IgG1 heavy chain constant region ($C_H$), wherein the fusion protein has the formula:

$$X_1\text{-}X_2\text{-}X_3\text{-}C_H\text{-}(X_4)_n\text{-}X_5$$

or has the formula:

$$X_3\text{-}C_H\text{-}X_2\text{-}X_1\text{-}(X_4)_n\text{-}X_5.$$

* * * * *

SEQUENCE LISTING

<160> NUMBER OF SEQ ID NOS: 5

<210> SEQ ID NO 1
<211> LENGTH: 6
<212> TYPE: PRT
<213> ORGANISM: Artificial sequence
<220> FEATURE:
<223> OTHER INFORMATION: Endoplasmic reticulum retention signal - SEKDEL

<400> SEQUENCE: 1

Ser Glu Lys Asp Glu Leu
1               5

<210> SEQ ID NO 2
<211> LENGTH: 4
<212> TYPE: PRT
<213> ORGANISM: Artificial sequence
<220> FEATURE:

```
<223> OTHER INFORMATION: Endoplasmic reticulum retention signal - KDEL

<400> SEQUENCE: 2

Lys Asp Glu Leu
1

<210> SEQ ID NO 3
<211> LENGTH: 4
<212> TYPE: PRT
<213> ORGANISM: Artificial sequence
<220> FEATURE:
<223> OTHER INFORMATION: Endoplasmic reticulum retention signal - HDEL

<400> SEQUENCE: 3

His Asp Glu Leu
1

<210> SEQ ID NO 4
<211> LENGTH: 10
<212> TYPE: PRT
<213> ORGANISM: Artificial sequence
<220> FEATURE:
<223> OTHER INFORMATION: alpha-helical linker

<400> SEQUENCE: 4

Glu Ala Ala Ala Lys Glu Ala Ala Ala Lys
1               5                   10

<210> SEQ ID NO 5
<211> LENGTH: 6
<212> TYPE: PRT
<213> ORGANISM: Artificial sequence
<220> FEATURE:
<223> OTHER INFORMATION: 6x His tag

<400> SEQUENCE: 5

His His His His His His
1               5
```